(12) United States Patent
Prasad et al.

(10) Patent No.: US 6,783,368 B2
(45) Date of Patent: Aug. 31, 2004

(54) TRANSIENT HEAT CONDUCTION USING THERMOCOUPLES, THERMOCHROMIC LIQUID CRYSTALS, AND NUMERICAL SIMULATION

(75) Inventors: Ajay K. Prasad, Newark, DE (US); Roger Stahl, Millington, MD (US)

(73) Assignee: University of Delaware, Newark, DE (US)

( * ) Notice: Subject to any disclaimer, the term of this patent is extended or adjusted under 35 U.S.C. 154(b) by 0 days.

(21) Appl. No.: 10/336,596

(22) Filed: Jan. 3, 2003

(65) Prior Publication Data

US 2003/0103548 A1 Jun. 5, 2003

Related U.S. Application Data

(62) Division of application No. 09/880,293, filed on Jun. 13, 2001, now abandoned.
(60) Provisional application No. 60/211,810, filed on Jun. 14, 2000.

(51) Int. Cl.[7] .............................................. G09B 23/16
(52) U.S. Cl. ...................................................... 434/276
(58) Field of Search ................................ 434/276, 298, 434/299, 300, 301, 302, 385; 374/43, 179, 162

(56) References Cited

U.S. PATENT DOCUMENTS

| | | | | |
|---|---|---|---|---|
| 2,272,245 A | * | 2/1942 | Kuck | 434/385 |
| 4,060,916 A | * | 12/1977 | Finigan et al. | 434/126 |
| 4,152,847 A | * | 5/1979 | Pfeiffer | 434/385 |
| 5,526,148 A | * | 6/1996 | Moffat et al. | 349/20 |
| 5,805,245 A | * | 9/1998 | Davis | 349/20 |
| 5,953,449 A | * | 9/1999 | Matsuda et al. | 382/162 |
| 6,585,408 B2 | * | 7/2003 | El-Gabry et al. | 374/43 |

* cited by examiner

*Primary Examiner*—Kurt Fernstrom
(74) *Attorney, Agent, or Firm*—Connolly Bove Lodge & Hutz LLP

(57) ABSTRACT

An apparatus to visually and electronically observe the transient temperature changes in a heat-conducting body, and a method for teaching heat conduction to students incorporating the apparatus. The apparatus includes a heat-conducting body, and a pair of electric strip heaters attached to adjacent sides of the heat-conducting body for conducting heat therethrough. A pair of heat exchangers are attached to sides of the heat-conducting body that are opposite to the sides the electric strip heaters are attached to. A thermochromic liquid crystal sheet is provided on a top surface of the heat-conducting body and displays the transient heat conduction through the heat-conducting body. An insulating plate is located above the top surface of the heat-conducting body to create a gap between the thermochromic liquid crystal sheet and the insulating plate. A plurality of thermocouples are attached to a bottom surface of the heat-conducting body for measuring the transient heat conduction within the heat-conducting body.

11 Claims, 2 Drawing Sheets

70a-70p

To frame grabber and computer

80

TLC Sheet-40
50
52
10
18
60

TRANSIENT HEAT CONDUCTION USING THERMOCOUPLES, THERMOCHROMIC LIQUID CRYSTALS, AND NUMERICAL SIMULATION

CROSS REFERENCE TO RELATED APPLICATIONS

This application is a divisional of U.S. patent application Ser. No. 09/880,293 filed 13 Jun. 2001, now abandoned which claims priority to U.S. provisional application Ser. No. 60/211,810, filed 14 Jun. 2000.

BACKGROUND OF THE INVENTION

A. Field of the Invention

The present invention relates to a novel device that provides a hands-on method to observe and record the time-varying temperature distribution within a heat-conducting body, such as a metal plate, using thermocouples and thermochromic liquid crystal sheet. The invention has applications for use in teaching students about transient heat conduction.

B. Description of the Related Art

Thermochromic liquid crystals ("TLCs") are organic long-chain molecules that have the useful property of being temperature sensitive. They respond to temperature by changing their molecular structure. The change in molecular structure causes changes in the wavelength of light that is reflected by the TLCs. The result is that the TLCs will change color in response to temperature. Contrary to conventional color representation of temperatures, TLCs will display a red color at low temperatures and a blue color at higher temperatures. During the transition from lower to higher temperatures, TLCs will display a spectrum of colors. TLCs are described in detail in U.S. Pat. No. 4,741,859, titled "Thermochromic liquid crystal materials and devices", issued May 1988, the disclosure of which is herein incorporated by reference.

TLCs are typically described with two criteria: (1) red start; and (2) color bandwidth. These criteria are commonly defined using degrees Celsius (° C.) values. Red start is the temperature at which color play commences. Color bandwidth is the temperature range over which the colors change from red to blue. TLCs can be obtained from various manufacturers with customized red start and color bandwidth values. TLCs can be in either a slurry form that can be added to a liquid flow, or in the form of a sheet. Common uses for TLCs are thermometers for aquariums and battery tester strips.

SUMMARY OF THE INVENTION

In teaching students the concept of heat conduction, the inventors have found that an apparatus capable of visually and electronically documenting the transient temperature changes in a heat-conducting body is an excellent tool. Thus, the present invention is directed towards such an apparatus and the method of using the apparatus in a student teaching exercise.

The present invention provides an apparatus to observe transient heat conduction in a heat-conducting body. The heat-conducting body can be in the form of a cube, plate, sphere or nearly any other form. The apparatus of the present invention may be used in a process to study one, two, or three dimensional heat flow in a teaching laboratory exercise. The invention is well-suited for use in schools to give students a hands-on experience with transient heat conduction. The present invention combines the results obtained from the teaching exercise using the apparatus with a numerical simulation of the transient heat conduction within the heat-conducting body of the apparatus and have the students make a comparison of the actual results with the numerically-simulated results.

Additional advantages of the invention will be set forth in part in the description which follows, and in part will be learned from the description, or may be learned by practice of the invention. The advantages of the invention will be realized and attained by means of the elements and combinations particularly pointed out in the appended claims.

In accordance with the purpose of the invention, as embodied and broadly described herein, the invention comprises a heat-conducting body that is heated on at least one surface and cooled on at least one surface. Within the heat-conducting body is a means to measure temperature, such as a plurality of thermocouples. Additionally, at least one surface of the heat-conducting body has a means to visually observe the temperature of the heat-conducting body, such as a sheet or covering of thermochromic liquid crystals ("TLCs"). A visual recordation means, such as a color charge-coupled device (CCD) camera, records the transient temperature changes displayed by the visual observation means to visually observe and record the temperature of the heat-conducting body.

In conducting the teaching laboratory experiment, the transient temperature changes within the heat-conducting body are observed using the output of both the means to measure temperature and the means to visually observe temperature. In a preferred embodiment of the invention, the means to measure temperature is performed by observing the transient output of the thermocouple array within or upon the heat-conducting body. Additionally, the transient temperature changes are observed using the means to visually observe temperature. In a preferred embodiment of the invention, the color changes of the TLC are observed. Use of the visual recordation means allows for a comparison of the observations of the means to measure temperature and the means to visually observe the temperature. A final exercise in the teaching laboratory is to compare the results obtained with the means to measure temperature and the means to visually observe temperature with a numerical simulation of the heat-conducting body.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate one embodiment of the invention and together with the description, serve to explain the principles of the invention. In the drawings.

DESCRIPTION OF THE PREFERRED EMBODIMENT

Reference will now be made in detail to the present preferred embodiment of the invention, an example of which is illustrated in the accompanying drawings. Wherever possible, the same reference numbers will be used throughout the drawings to refer to the same or like parts.

The invention is directed to an apparatus to observe the transient heat conduction within a heat-conducting body. The invention is also directed to a process of using the apparatus to observe the transient heat-conduction in the heat-conducting body to conduct a student teaching laboratory experiment.

Figure 4:
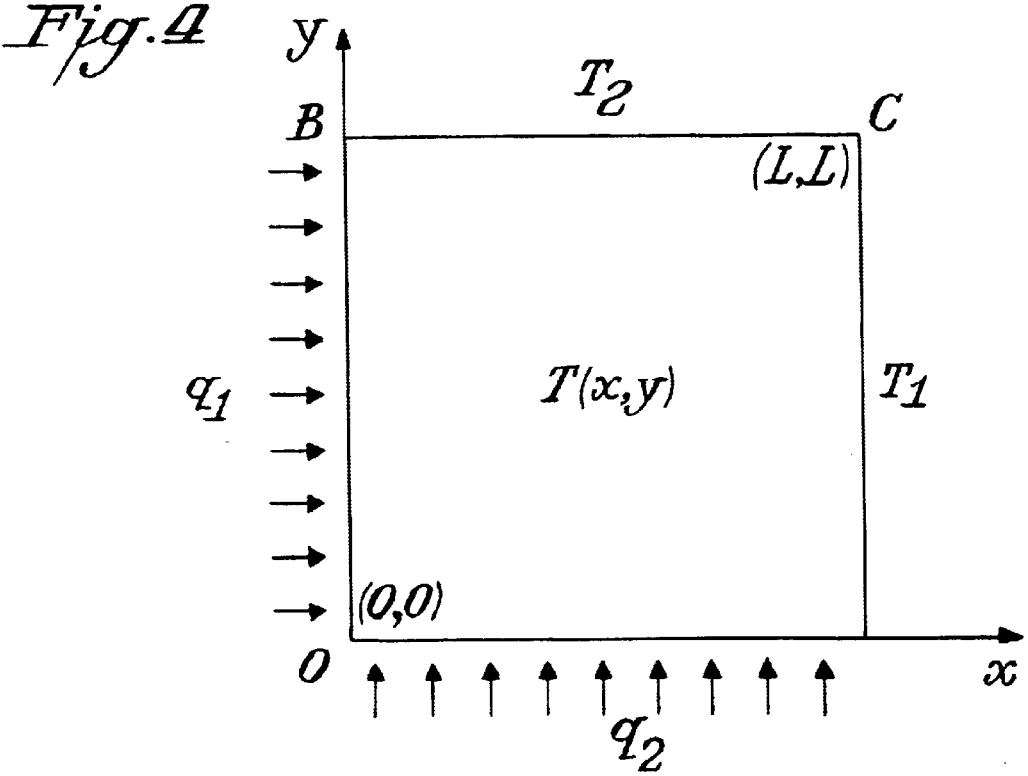
FIG. 4 is a schematic of the geometry and boundary conditions for a two-dimensional heat-conducting body used in the apparatus shown in FIG. 1.

In a preferred embodiment of the present invention, the heat-conducting body is configured to have essentially two-dimensional heat flow. In this embodiment, the heat-conducting body resembles a heated plate. FIG. 4 shows a diagram of the geometry and boundary conditions for the two-dimensional heated plate. In this configuration, the time-dependent temperature of the heat-conducting body is defined as:

$$T=T(x,y,t)$$

Under steady-state conditions, the time dependance will disappear. The temperature dependence in the z direction is eliminated, provided the top and bottom surfaces of the heat-conducting body are well insulated. The preferred embodiment of the present invention provides such insulating boundary conditions. Using the diagram in FIG. 4, one can solve for the time-dependent temperature, T(x, y, t), subject to the following initial conditions:

$$T(x,y,0)=T_0$$

$$q(0, y, t) = -k\frac{\partial T(0, y, t)}{\partial x} = q_1$$

$$q(x, 0, t) = -k\frac{\partial T(x, 0, t)}{\partial y} = q_2$$

$$T(L,y,t)=T_1$$

$$T(x,L,t)=T_2$$

where k is the thermal conductivity of the heat-conducting body. Temperatures $T_1$ and $T_2$ are assumed to be equal to the temperature of the cooling water in the two heat exchangers, while $q_1$ and $q_2$ may be obtained from the power rating of the electrical strip heaters (described in more detail below). Temperature $T_0$ is known from the measurements taken by the thermocouples (described in more detail below). Therefore, in a two-dimensional heated plate embodiment, all four boundary conditions and initial conditions are completely determined and can be used to solve for the temperature distribution within the two-dimensional plate. To determine the temperature distribution, the heat conduction law may be written as:

$$\nabla^2 T = \frac{\partial^2 T}{\partial x^2} + \frac{\partial^2 T}{\partial y^2} = \frac{1}{\alpha}\frac{\partial T}{\partial t} \quad (1)$$

where α is the thermal diffusivity of the plate. For the steady-state condition, all time-derivatives are set to zero and the right-hand side of Equation 1 becomes zero.

Figure 1:
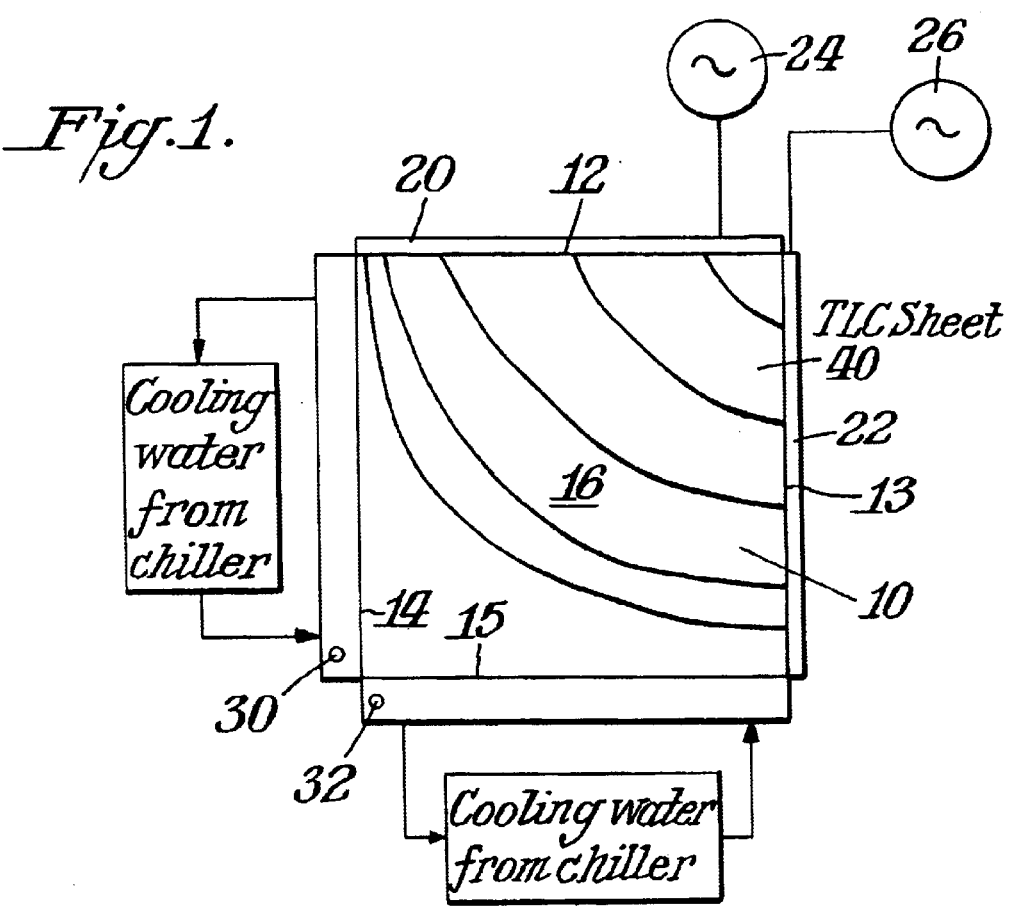
FIG. 1 is a top view of an apparatus for observing and measuring transient heat conduction in accordance with an embodiment of the present invention.

A preferred embodiment of the apparatus is shown in FIG. 1. The apparatus comprises a heat-conducting body 10. In the illustrated embodiment, the heat-conducting body 10 is a metal plate, and more preferably, is an aluminum plate. In the illustrated embodiment shown in FIG. 1 the aluminum plate heat-conducting body 10 is approximately twelve inches long, twelve inches wide, and two inches thick.

In the illustrated embodiment shown in FIG. 1, two electric strip heaters 20, 22 are attached to adjacent sides 12, 13 of the heat-conducting body. A preferred embodiment of the present invention uses two electric strip heaters measuring two inches wide and twelve inches long and are rated 10 W/in$^2$ (Model No. KH-212 from Omega Engineering). Also in a preferred embodiment of the invention and shown in FIG. 1, Variacs 24, 26 operating at 12 amps, 120 volts AC (VAC) are electrically connected to electrical strip heaters 20, 22. A Variac is an adjustable voltage regulator that adjusts the voltage supplied to electrical strip heaters 20, 22.

Referring still to the illustrated embodiment shown in FIG. 1, two heat exchangers 30, 32 are attached to the sides 14, 15 of the heat-conducting body opposite the electric strip heaters 20, 22. The electric strip heaters 20, 22 and heat exchangers 30, 32 are attached using a means known in the art to provide a thermal connection to the heat-conducting body 10. In a preferred embodiment, the electric strip heaters 20, 22 are attached to the heat-conducting body 10 using thermal cement and the heat exchangers 30, 32 are bolted to the heat-conducting body 10 with heat sink grease used to enhance heat transfer between the heat-conducting body 10 and the electric strip heaters 20, 22.

In the illustrated embodiment shown in FIG. 1, a thermochromic liquid crystal ("TLC") sheet 40 is attached to the top surface 16 of the heat-conducting body 10. In a preferred embodiment of the present invention, the TLC sheet 40 (available from Hall Crest, Inc. Glenview, Ill.) has an adhesive backing and is attached directly to the top surface of the heat-conducting body 10. Also in a preferred embodiment of the present invention, the TLC sheet 40 has a temperature range of at least 5° C.

The illustrated embodiment shown in FIG. 1 has a substantially transparent insulating plate 50 located above the top surface 16 of the heat-conducting body 10. In the illustrated embodiment shown in FIG. 3, the insulating plate 50 is located a small distance above the top surface 16 of the heat-conducting body 10 creating an air gap 52. In the preferred embodiment of the present invention, the air gap 52 insulates the heat-conducting body 10 and restricts or substantially prevents heat conduction through the top surface 16 of the heat-conducting body 10. In a currently-preferred embodiment of the present invention, the substantially transparent insulating plate 50 is made of Pyrex.

Figure 3:
FIG. 3 is a side view of the apparatus shown in FIG. 1.
Figure 3:
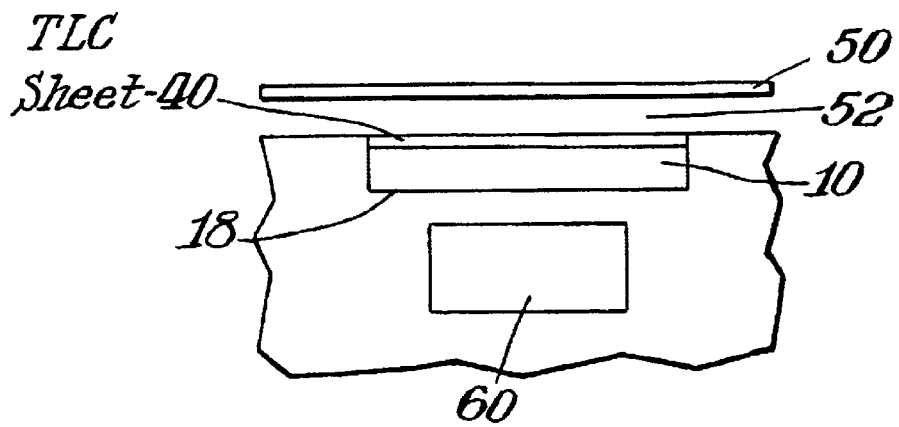

Still referring to the illustrated embodiment shown in FIG. 3, the bottom surface 18 of the heat-conducting body 10 is supported on an insulating material 60. In a preferred embodiment of the present invention, the insulating material 60 restricts or substantially prevents heat conduction through the bottom surface 18 of the heat-conducting body 10. It is a preferred embodiment of the present invention that the insulating material 60 is able to support the heat-conducting body 10 and not conduct heat. In a currently-preferred embodiment, the insulating material 60 is glass wool. The insulating material 60 can also be any other material known to be suitable for this purpose such as, but not limited to, expanded polystyrene pellets ("packing peanuts"), expanded starch pellets, and melamine foam.

Figure 2:
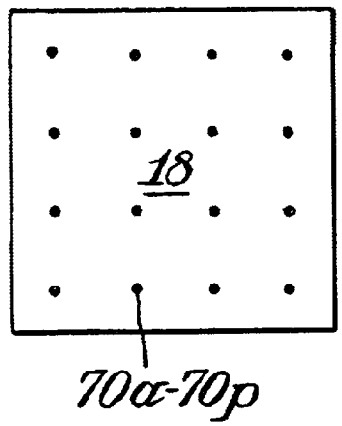
FIG. 2 is bottom view of the apparatus shown in FIG. 1.

Attached to the heat-conducting body 10 is a means to measure the transient temperature changes within the heat-conducting body. In the illustrated embodiment shown in FIG. 2 the means to measure the transient temperature changes is an array of thermocouples 70. The array of thermocouples 70 comprises of a plurality of individual thermocouples 70a–70p. In a preferre embodiment the individual thermocouples 70a–70p are arranged in a grid; the thermocouples 70a–70p are spaced equidistant to one another and/or the edges of the bottom surface 18 of the heat-conducting body 10. The individual thermocouples 70a–70p have a temperature range suitable for measuring the transient temperature changes based on the composition of the heat-conducting body 10, the power of the electric strip heaters 20, 22 and the cooling rate of the heat exchangers 30, 32. In a preferred embodiment of the present invention, the individual thermocouples 70a–70p are 24-gauge, Type K, Teflon-coated termocouples (Model No. 5TC-TT-K-24-36, from Omega Engineering).

In a preferred embodiment, located above the top surface of the heat-conducting body is a means to visually record the transient temperature changes indicated by the TLC. In the illustrated embodiment shown in FIG. 3, the means to visually record transient temperature changes is a color CCD camera 80. Not shown in FIG. 3, but included in the same preferred embodiment, is a frame-grabber which captures the pictures taken with the color CCD camera 80.

The inventors have found that the above-described apparatus of the present invention can be used in a novel student teaching laboratory exercise. In a preferred embodiment, the laboratory exercise comprises the steps of selecting a temperature and heat flux boundary conditions for the heat-conducting body 10, then recording the temperature readings using the thermocouples 70a–70p, and then capturing the TLC color play with the color CCD camera 80 and frame grabber.

In a preferred embodiment of the present invention, the students will first record the initial temperature of the heat-conducting body 10 by measuring the output of the thermocouples 70a–70p. The students will also take pictures of the TLC color play using the color CCD camera 80 and the frame grabber. This data provides the initial conditions for a numerical simulation portion of the laboratory exercise.

Next, the students select heat exchanger temperatures to set the boundary conditions for $T_1$ and $T_2$. In a preferred embodiment, the heat exchanger temperatures are both set to 20° C.

Next, the students adjust the power supplied to the electric strip heaters 20, 22 via the two Variacs 24, 26. The heating power from each strip heater 20, 22 corresponds to the values for $q_1$ and $q_2$. The object of the teaching exercise is to obtain maximum color play of the TLC 40. In a preferred embodiment, the Variacs 24, 26 will be set between seventy and eighty volts (V). In a currently-preferred embodiment, where the resistance of each electric strip heater 20, 22 is 57.5 ohms, the students can determine the power, P, supplied by the heaters 20, 22 using the formula:

$$P = \frac{V^2}{R}$$

where P is power, V is volts, and R is the resistance of the strip heaters 20, 22. The heat flux q can be determined using the formula:

$$q = \frac{P}{A}$$

where A is the area of the portion of the heat-conducting body 10 that the electric strip heater is attached to. This computation is based on the assumption that all of the power generated by the electric strip heaters 20, 22 is directed into the plate.

When the heat-conducting body 10 reaches steady state, in a preferred embodiment of the invention, the students record the temperatures measured by each of the thermocouples 70a–70p in the thermocouple array 70. In a preferred embodiment, the temperature of each thermocouple 70a–70p is measured individually by using a multiposition switch. In another preferred embodiment, the temperature of every thermocouple 70a–70p is measured simultaneously. Contemporaneous with each thermocouple measurement, either individually or simultaneously, the students capture a video image of the TLC. In a preferred embodiment, the students use color CCD camera 80 and frame grabber. The students record the time that each thermocouple measurement and frame grab is performed.

The laboratory exercise may be terminated when the heat-conducting body 10 reaches steady state. This is determined by measuring the temperature using the thermocouples 70a–70p and verifying that the temperature of the heat-conducting body 10 is no longer changing with time.

In a preferred embodiment, once the data is collected, the students plot the temperature contours obtained from the thermocouple readings to show the time-varying trends. The temperature plots may be made using any variety of plotting means, including computer plotting programs that can render contour plots in color. Additionally, the students may plot temperature as a function of time for a selected number of individual thermocouples.

In a preferred embodiment, the students compare the temperature contour plots with the color printouts of images of the TLC obtained with the means to visually observe temperature. In a preferred embodiment, the images are color prints of the frames grabbed using the color CCD camera 80 and the frame grabber.

In a preferred embodiment, the students perform an unsteady state numerical solution using the boundary and initial conditions used in the laboratory exercise. The students then compare the results of the numerical solution with the values obtained from the thermocouple measurements and the TLC pictures.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method for teaching heat conduction, comprising:
   providing an apparatus having:
      a heat-conducting body,
      at least one heater attached to one side of said heat-conducting body for conducting heat through said heat-conducting body,
      at least one heat exchanger attached to a side of said heat-conducting body that is opposite to the side said heater is attached to,
      a thermochromic liquid crystal sheet attached to a top surface of said heat-conducting body, wherein the color of the thermochromic liquid crystal sheet varies due to the transient heat conduction through said heat-conducting body,
      an insulating plate located above the top surface of said heat-conducting body to create a gap between said thermochromic liquid crystal sheet and said insulating plate,
      a plurality of thermocouples attached to a bottom surface of said heat-conducting body for measuring the transient heat conduction within said heat-conducting body, and
      means to record the transient heat conduction within the heat-conducting body;

selecting a temperature and heat flux boundary conditions for the heat-conducting body;

recording the temperatures of portions of the heat-conducting body using the plurality of thermocouples;

recording the colors displayed by the thermochromic liquid crystal sheet with the means to record the transient heat conduction; and terminating the method when the temperature of the heat-conducting body is no longer changing with time.

2. A method for teaching heat conduction as recited in claim 1, wherein the heat flux boundary conditions are set by setting the temperature of the heat exchanger.

3. A method for teaching heat conduction as recited in claim 1, wherein the step of recording the temperatures of portions of the heat-conducting body comprises measuring the temperatures recorded by the plurality of thermocouples.

4. A method for teaching heat conduction as recited in claim 1, wherein the step of recording the temperatures of portions of the heat-conducting body and the step of recording the colors displayed by the thermochromic liquid crystal sheet are performed simultaneously.

5. A method for teaching heat conduction as recited in claim 1, further comprising:

plotting the temperature contours obtained from the temperatures recorded by the plurality of thermocouples; and comparing the temperature contours with recorded colors of the thermochromic liquid crystal sheet.

6. A method for teaching heat conduction, comprising:

providing an apparatus having:

a heat-conducting body having four sides, two heaters attached to adjacent sides of said heat-conducting body for conducting heat through said heat-conducting body, two heat exchangers attached to sides of said heat-conducting body, wherein each heat exchanger is attached to a side of the heat-conducting body that is opposite to the side of the heat-conducting body that the corresponding heater is attached to, a thermochromic liquid crystal sheet attached to a top surface of said heat-conducting body, wherein the color of the thermochromic liquid crystal sheet varies due to the transient heat conduction through said heat-conducting body, an insulating plate located above the top surface of said heat-conducting body to create a gap between said thermochromic liquid crystal sheet and said insulating plate, a plurality of thermocouples attached to a bottom surface of said heat-conducting body for measuring the transient heat conduction within said heat-conducting body, and means to record the transient heat conduction within the heat-conducting body;

selecting a temperature and heat flux boundary conditions for the heat-conducting body;

recording the temperatures of portions of the heat-conducting body using the plurality of thermocouples; and recording the colors displayed by the thermochromic liquid crystal sheet with the means to record the transient heat conduction.

7. A method for teaching heat conduction as recited in claim 6, wherein the heat flux boundary conditions are set by setting the temperature of one or both of the heat exchangers.

8. A method for reaching heat conduction as recited in claim 6, wherein the step of recording the temperatures of portions of the heat-conducting body comprises measuring the temperatures recorded by the plurality of thermocouples.

9. A method for teaching heat conduction as recited claim 6, wherein the step of recording the temperatures of portions of the heat-conducting body and the step of recording the colors displayed by the thermochromic liquid crystal sheet are performed simultaneously.

10. A method for teaching heat conduction as recited in claim 6, further comprising:

terminating the method when the temperature of the heat-conducting body is no longer changing with time.

11. A method for teaching heat conduction as recited in claim 6, further comprising:

plotting the temperature contours obtained from the temperatures recorded by the plurality of thermocouples; and comparing the temperature contours with recorded colors of the thermochromic liquid crystal sheet.

* * * * *

UNITED STATES PATENT AND TRADEMARK OFFICE
CERTIFICATE OF CORRECTION

PATENT NO. : 6,783,368 B2
DATED : August 31, 2004
INVENTOR(S) : Ajay K. Prasad et al.

It is certified that error appears in the above-identified patent and that said Letters Patent is hereby corrected as shown below:

<u>Column 8,</u>
Line 23, "reaching" should read -- teaching --.

Signed and Sealed this

Fifteenth Day of February, 2005

JON W. DUDAS
*Director of the United States Patent and Trademark Office*